(12) United States Patent
Berndt et al.

(10) Patent No.: US 10,466,222 B2
(45) Date of Patent: Nov. 5, 2019

(54) METHOD FOR OPERATING A TEST STATION FOR PORTABLE GAS-MEASURING DEVICES AS WELL AS TEST STATION FOR PORTABLE GAS-MEASURING DEVICES

(71) Applicant: Dräger Safety AG & Co. KGaA, Lübeck (DE)

(72) Inventors: Malte Berndt, Lübeck (DE); Christof Rodehorst, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 443 days.

(21) Appl. No.: 15/386,564

(22) Filed: Dec. 21, 2016

(65) Prior Publication Data

US 2017/0184558 A1 Jun. 29, 2017

(30) Foreign Application Priority Data

Dec. 23, 2015 (DE) .................. 10 2015 016 828

(51) Int. Cl.
G01N 33/00 (2006.01)
G01M 99/00 (2011.01)
G01M 3/26 (2006.01)

(52) U.S. Cl.
CPC ............ G01N 33/007 (2013.01); G01M 3/26 (2013.01); G01M 99/00 (2013.01); G01N 33/0006 (2013.01); *G01N 2033/0072* (2013.01)

(58) Field of Classification Search
CPC ............ G01N 33/007; G01N 33/0006; G01N 2033/0072; G01N 27/4175; G01N 27/4163; G01M 99/00; G01M 3/26
See application file for complete search history.

(56) References Cited

U.S. PATENT DOCUMENTS

| 4,267,030 A | 5/1981 | Breuer et al. |
| 2014/0331737 A1 | 11/2014 | Kaneblei et al. |
| 2014/0342459 A1* | 11/2014 | Berndt ............... G01N 31/10 436/37 |

FOREIGN PATENT DOCUMENTS

| CH | 624 488 A5 | 7/1981 |
| DE | 10 2012 210 090 B4 | 1/2014 |
| DE | 10 2013 008 425 B3 | 5/2014 |

* cited by examiner

*Primary Examiner* — Daniel S Larkin
*Assistant Examiner* — Anthony W Megna Fuentes
(74) *Attorney, Agent, or Firm* — McGlew and Tuttle, P.C.

(57) ABSTRACT

A method for operating a test station (10) for portable gas-measuring devices (20) is provided. The gas-measuring device (20) is arranged in fluid-communication with the test station (10) via at least one interface (13). A flow time is set, during which the test gas (30) is fed and a waiting time is set, during which no test gas (30) is fed. After an end of the feed of the at least one test gas results of the test are analyzed. The test station (10) is configured for feeding at least one test gas (30) to the interface (13). The test station (10) for portable gas-measuring devices (20) has at least one interface (13) for the fluid-communicating arrangement of the gas-measuring device (20), and wherein the test station (10) is configured for feeding at least one test gas (30) to the interface (13).

16 Claims, 5 Drawing Sheets

METHOD FOR OPERATING A TEST STATION FOR PORTABLE GAS-MEASURING DEVICES AS WELL AS TEST STATION FOR PORTABLE GAS-MEASURING DEVICES

CROSS REFERENCE TO RELATED APPLICATIONS

This application claims the benefit of priority under 35 U.S.C. § 119 of German Application 10 2015 016 828.2 filed Dec. 23, 2015, the entire contents of which are incorporated herein by reference.

FIELD OF THE INVENTION

The present invention pertains to a method for operating a test station for portable gas-measuring devices. The present invention pertains, further, to a test station for portable gas-measuring devices.

BACKGROUND OF THE INVENTION

Gas-measuring devices and especially portable gas-measuring devices are used in many different ways in modern technology. A certain and reliable detection of especially toxic and/or explosive gases, for example, $CH_4$, $O_2$, CO, $H_2S$, $SO_2$, $NO_2$ and/or NO is a decisive criterion for an error-free functioning of such a gas-measuring device. Test stations are used for portable gas-measuring devices to test the ability of the gas-measuring devices to detect substances and/or to recalibrate and readjust the gas-measuring devices. Such test stations are known, for example, from DE 10 2012 210 090 B4 and US 2 014 331 737 A1. To test as well as to calibrate and adjust the gas-measuring device, the gas-measuring device is connected to the test station, and at least one test gas is fed by the test station to the gas-measuring device for the detection. A response or reaction of the gas-measuring device to the fed test gas is then analyzed by the test station and/or the gas-measuring device and the gas-measuring device is classified, for example, as defective or okay.

It is known in prior-art test stations for portable gas-measuring devices that the particular test gas being used is fed in a steady flow to the gas-measuring device to be tested. In particular, this gas flow is maintained in prior-art test stations until the gas-measuring device has met a test criterion or until a time is reached at which a defective behavior of the gas-measuring device becomes obvious. A large amount of the test gas being used is consumed in this manner. Since the test gases used are often very expensive, this may lead to high costs in connection with the testing, calibration and adjustment of portable gas-measuring devices by test stations.

SUMMARY OF THE INVENTION

Based on this state of the art, a basic object of the present invention is to at least partly eliminate these drawbacks during the operation of test stations for portable gas-measuring devices and in test stations for portable gas-measuring devices. An object of the present invention is to provide a method for operating a test station for portable gas-measuring devices as well as a test station for portable gas-measuring devices, which make it possible to reduce the consumption of test gas during the testing, calibration and adjustment of portable gas-measuring devices by the test station in an especially simple and favorable manner.

According to a first aspect of the present invention, the object is accomplished by a method for operating a test station for portable gas-measuring devices, wherein the test station has at least one interface for the fluid-communicating arrangement of the gas-measuring device and wherein the test station is configured for feeding at least one test gas to the interface. A method according to the present invention has the following steps:

a) Arranging the gas-measuring device at the interface and detecting a type of the gas-measuring device to be tested by the test station, b) setting of a flow time, during which the test gas is fed through the test station, and of a waiting time, during which no test gas is fed, based on a result of the detection of the gas-measuring device to be tested according to step a), c) starting a feed of the at least one test gas for feeding the test gas via the interface to the gas-measuring device during the flow time through the test station;

d) after the end of the flow time and the conclusion of the feed of the at least one test gas, starting of the waiting time as well as performing a measurement for detecting the fed test gas by the gas-measuring device at least prior to the end of the waiting time, and e) analyzing the results of the measurement carried out in step d) by the test station and/or by the gas-measuring device.

A test station for portable gas-measuring devices can be operated by a method according to the present invention. Such a test station has at least one interface, and the interface can make it possible to arrange the gas-measuring device in a fluid-communicating manner. A fluid communicating configuration (a fluid-communicating means) in the sense of the present invention relates especially to a gas, especially a test gas, flowing between the test station and a gas-measuring device arranged at the interface. The interface may preferably act as a physical, fluid and electrical (signal) coupling, which can make it possible to arrange the gas-measuring device at the test station in a reliable manner. Provisions may, for example, also be made for the interface to have sealing elements for sealing the connection between the interface and the gas-measuring device. Further, a test station may have a plurality of such interfaces, so that a plurality of gas-measuring devices may also be arranged at the test station. Further, the test station may feed at least one test gas to the interface. Depending on the configuration of the test station, it is also possible to feed a plurality of test gases to the interface, both one after another and simultaneously. The at least one test gas can be fed automatically to the gas-measuring device to be tested due to the fluid-communicating arrangement of the gas-measuring device at the interface.

In a first step a), the gas-measuring device is arranged at the interface of the test station. As a result, a fluid-communicating connection is established between the gas-measuring device and the interface. The gas-measuring device is preferably arranged in this case at the interface such that, in particular, a sensor of the gas-measuring device is arranged in this fluid-communicating connection, so that the test gas can be fed in the further course especially to the sensor of the gas-measuring device. Further, via an electrical connection (at the interface) between the gas-measuring device and a control unit of the test station, a particular type of the gas-measuring device to be tested is detected by the test station in step a) of a method according to the present invention. The arrangement and the detection during step a)

of the method according to the present invention may take place simultaneously or in any desired order. In particular, the course of the test to be performed can be set by the detection of the type of the gas-measuring device to be tested.

This may be carried out especially in a step b) of the method according to the present invention. Based on a result of the detection, especially of the type of the gas-measuring device to be tested, a flow time and a waiting time are set in this step b). The flow time is defined in the sense of the present invention as the time during which a test gas is fed through the test station. Such feed comprises here especially the transport of the test gas from a storage tank, for example, a gas cylinder, via a feed line to the interface. The setting of the flow time means in the sense of the present invention especially the same as the setting of a quantity of test gas to be fed, which will then require a certain time for being fed to the interface. The flow time and such a fed quantity may be linked and therefore able to be converted into one another, for example, via a flow velocity of the test gas and/or a mass flow of test gas. A time during which no feed of the test gas is carried out is defined by the waiting time. A response of the gas-measuring device is waited for during this waiting time. The waiting time is also often called idle time. Thus, a test gas is also not consumed by the test station during this waiting time, even though a response of the gas-measuring device is or can be analyzed at the same time. Due to the detection of the particular type of the gas-measuring device to be tested in step a) of the method according to the present invention, an adapted flow time or waiting time can be set for the particular detected type in step b). It is possible as a result to set the flow time and the waiting time in an especially need-adapted and need-based manner.

Feed of the at least one test gas is started in the next step c) of a method according to the present invention. The test gas is preferably fed to the test station through this feed, which may be carried out, for example, by a feed device of the test station. The feeding of the test gas via the interface to the gas-measuring device, made possible especially by the fluid-communicating connection established during the arrangement in step a) between the interface and the gas-measuring device to be tested, can be provided hereby. The feed of the at least one test gas is carried out according to the present invention during the duration of the flow time and is concluded after the end of the flow time. Since the flow time in step b) of the method according to the present invention was set such that it is long enough for the feed of test gas to the interface, it is usually possible hereby to also achieve the feeding of the test gas to the gas-measuring device via the fluid-communicating connection of the interface and the gas-measuring device after the end of the flow time.

The waiting time is started in step d) of the method according to the present invention after the end of the flow time and, as a result, also after the end of the feed of the at least one test gas. This start of the waiting time may be provided especially preferably after the end of the flow time. Further, a measurement is carried out for detecting the fed test gas by the gas-measuring device. This measurement is usually carried out at least before the end of the waiting time. The measurement may be carried out at any time during the waiting time, for example, also at the very end of the waiting time shortly before the end of this waiting time. The duration of the measurement in time may be shorter than the total waiting time. It is also possible to perform repeated measurements for the duration of the waiting time. As an alternative, a performed measurement may also be performed for the entire duration of the waiting time. Due to the performance of the measurement(s) being limited in time to the duration of the waiting time, it can be ensured that the gas-measuring device is capable of performing the detection of the fed test gas in a preset time, especially within the waiting time. The waiting time was preferably selected for this purpose in step b) such that detection of the fed test gas by a functioning gas-measuring device is to be expected. A defective gas-measuring device can be detected with certainty in this manner if no detection of the test gas by the gas-measuring device to be tested has taken place after the end of the waiting time despite the measurement having been performed.

Finally, the measurement results of the measurement carried out in step d) are analyzed in a final step e) of the method according to the present invention. The analysis may be carried out in the test station, but preferably by the gas-measuring device itself. It can be detected now, in particular, whether the fed test gas was detected by the gas-measuring device. As a result, it can be determined whether or not the gas-measuring device is functioning.

In summary, the consumption of test gas can be markedly reduced by the method according to the present invention during the operation of a test station for portable gas-measuring devices. It can be made possible especially by the fact that the test gas is only fed during the flow time. In particular, test gas is fed only until it has reached the interface of the test station and has filled same. Feed of the test gas is concluded at this time, especially at the end of the flow time. The response of the measuring device to the fed test gas is then waited for during the waiting time, during which no test gas is being consumed any more. The cost of operating a test station for portable gas-measuring devices can also be reduced, in particular, due to this marked reduction on the test gas consumption.

Further, provisions may preferably be made in the method according to the present invention for at least one of the following features to be detected in connection with the detection of the type of the gas-measuring device to be tested in step a):

at least one sensor of the gas-measuring device, the response characteristic of the at least one sensor of the gas-measuring device, the state of aging of the at least one sensor of the gas-measuring device, and the test gas needed and/or used.

Based on the type of the gas-measuring device to be tested, which is to be detected in step a), the flow time and the waiting time are set in step b) of the method according to the present invention. For example, as a part of the type of the gas-measuring device to be tested, the at least one sensor of the gas-measuring device, which sensor is to be tested, may already affect the times to be set. In particular, it can be taken into account in this connection that a gas-measuring device may have a plurality of sensors, which may, in turn, be configured for detecting a plurality of different gases. For example, the sensors of gas-measuring devices may thus be based on different detection methods, for example, on a physical or chemical reaction, for detecting gases, A detection, for example, that of chlorine, may also take place only after saturation of the sensor, whereas such a saturation is not necessary in case of other gases and the detection can therefore take place more rapidly. In particular, these detection methods may also differ within one sensor if different gases can be detected by the sensor. These different detection methods may differ, for example, by the needed quantity of test gas that is necessary for a successful detection. This can be taken into account when setting the flow time and the waiting time in step b) of a method according to the present invention. A response characteristic, i.e., the time that a sensor of a gas-measuring device needs to detect a certain test gas that is present, may also affect the needed flow time or waiting time. It can be taken into account, in particular, that the response characteristic as part of the detection process should take place during the waiting time, because the response starts only when test gas is present in the area surrounding the sensor of the gas-measuring device. Feed of the test gas may preferably already have been concluded by this time. This can be taken into account in a reduction of the duration of the flow time. The state of aging of the at least one sensor of the gas-measuring device may also affect especially the response characteristic. In particular, the response characteristic of the at least one sensor may change, for example, become longer especially in time, over the course of use of the gas-measuring device. This can be taken into account when setting the flow time and especially the waiting time. A needed and/or used test gas may also represent a part of the type of the gas-measuring device to be tested, especially in case of test stations that can provide a plurality of test gases and/or in case of measuring devices that can detect a plurality of gases. For example, different flow times that are needed for the feed of the particular test gas being used from the storage tank to the interface may arise now especially in case of test gases that are fed from different storage tanks. Further, the concentration of the test gas being used may affect the rapidity with which it can be detected by a sensor of a gas-measuring device. Further, the form in which the test gas is present may also lead to a faster or slower detection by a sensor of the gas-measuring device. For example, test gases present in the vapor form are usually detected more slowly than test gases that are present in the gaseous form. This list is also incomplete, so that even further features can be detected for describing a type of the gas-measuring device to be tested, as a result of which it may become possible to set a flow time or a waiting time in an even more specific manner.

Further, provisions may preferably also be made in a method according to the present invention for taking into account a configuration of the test station and/or a state of the test station when setting the flow time and the waiting time in step b). For example, the length of feed lines, especially to different storage tanks of test gases, may also be taken into account, in particular, by the configuration. For example, a longer flow time may thus be necessary in case of long feed lines, for example, if the storage tanks of the test gases are arranged at a distance from the test station, than in case of short feed lines, if the storage tanks of the test gases are located close to the test station. Adsorption effects in the feed lines, which effects are, in turn, different for different types of test gases, may also affect the flow time, and a material used for the particular feed line should also be taken into account in this connection. A state of the test station may be defined especially as a previous operation of the test station. It can be taken into account, for example, that a test gas was likewise used in a most recently performed test of another gas-measuring device. If the same test gas is to be used for the gas-measuring device to be currently tested, it can thus be taken into account that the feed lines are already filled with the test gas. A flow time may be selected as an especially short flow time in this case. If, by contrast, the test gas is changed compared to the last time a test was performed, a markedly longer flow time may be needed to feed the needed test gas to the interface. In summary, it may become possible to set a flow time or a waiting time even better by taking into account the configuration and/or the state of the test station.

A method according to the present invention may especially preferably also be configured such that the measurement is carried out by the gas-measuring device at least partly already during the performance of step c). The test gas is fed through the test station to the interface during step c). By starting the measurement already during this step c), it is possible to avoid, for example, a time delay between the end of the flow time and the start of the measurement or the start of the waiting time. A method according to the present invention can thus be carried out even more rapidly.

Moreover, provisions may be made in the method according to the present invention for the measurement results to be compared with at least one reference value during the analysis in step e). By making this comparison with a reference value, for example, a legal requirement, it is possible to make a decision on whether the tested gas-measuring device operates properly. For example, a test gas concentration determined by the gas-measuring device can be compared with a test gas concentration that was provided by the test station. This may be via data stored in a memory associated with the control unit. A response time, i.e., the time that the gas-measuring device needs to detect a test gas that is present, may also be compared with a reference value. On the whole, especially good and comprehensible information can be obtained on the state of the gas-measuring device by such a comparison.

Provisions may be made in a variant of the method according to the present invention for the gas-measuring device to be marked as being defective in case of a negative result of the comparison in step e). A negative result may be, for example, a lack of response to the test gas, excessively slow detection of the test gas or detection of a too small quantity of the test gas by the gas-measuring device. In case of a gas-measuring device with such results, it is no longer possible to ensure reliable detection of a gas that corresponds to the test gas during the use of that gas-measuring device. A "defective" marking makes it possible to warn against the use of this gas-measuring device and especially to ensure hereby that the use of that device is prevented.

According to an especially preferred alternative variant, a method according to the present invention may be configured such that the following steps are carried out if the comparison in step e) has a negative result:

f) setting of a test time during which the test gas is fed through the test station, g) start of feed of at least one test gas through the test station to feed the test gas via the interface to the gas-measuring device for the duration of the test time through the test station, h) carrying out of a measurement to detect the fed test gas by the gas-measuring device during the test time, especially for the duration of the test time, and i) analysis of the results of the measurement carried out in step h).

In case of a negative result of the comparison in step e), the test station performs especially a test of a gas-measuring device in which the gas-measuring device detected no or too little test gas. Such a result may also occur in case of a functioning gas-measuring device if the flow time set in step b) was too short. No or at least too little test gas would have been fed in this case to the interface and thus via the fluid-communicating connection to the gas-measuring device in step c). A repeated testing of the gas-measuring device can be carried out by steps f) through I) according to this variant of a method according to the present invention, and continuous feed or flow of test gas is provided during this test. A test time during which the test gas shall be fed through the test station is set in the first step f). The test time may be determined, for example, as a sum of the flow time and waiting time set in step b). It is also possible to set the test time in another manner, especially as a longer test time. The test gas is fed in steps g) and h) and is fed to the gas-measuring device via the interface to the gas-measuring device. A measurement is carried out by the gas-measuring device, simultaneously during some phases, to detect the test gas being fed. Finally, an analysis of the results of the measurement carried out in step h) is carried out in step I). Such an analysis may, in turn, comprise a comparison with reference values. In case of a successful detection of the test gas by the gas-measuring device, especially in respect to the response time and/or concentration, the gas-measuring device can be characterized as functioning. If the result of the analysis of measurement results continues to be negative, the gas-measuring device can be marked as defective. Due to steps g) and h) being limited in time to the duration of the test time, an excessively prolonged performance of steps g) and h) can be prevented from occurring in case of an actually detective gas-measuring device. An excessive increase in test gas consumption can be avoided thereby. On the whole, rejection of functioning gas-measuring devices as defective devices, which can be attributed to the setting of an excessively short flow time, can be prevented by steps f) through i).

Further, a method according to the present invention may be perfected such that the test time set in step f) and a result of the analysis performed in step I) are taken into account when setting the flow time and the waiting time in step b). If the result of the analysis performed in step i) is positive, a sufficient quantity of test gas could be fed to the interface during the test time and successful detection of the fed test gas could be performed by the gas-measuring device to be tested. The flow time and the waiting time are set in step b) of a method according to the present invention, and the test time set in step f) can also be taken into account in case of a positive result of the analysis in step i). Adaptation especially of the flow time to different locations of installation of a test station operated by a method according to the present invention, which locations may differ especially by different lengths of feed lines, can be achieved hereby. As a result, it is possible to take into account, for example, the time at which the test station was newly installed and/or, for example, the lengths of feed lines between storage tanks of the test gases and the test station changed. On the whole, an iterative determination of the flow time and/or of the waiting time and, as a result, an especially need-adapted setting of the flow time and/or of the waiting time may thus also be made possible. Provisions may preferably be made in case of such an iterative determination for at least steps g) through i) to be carried out with a plurality of different gas-measuring devices. Incorrect determination of the flow time and/or of the waiting time based on an accidentally defective gas-measuring device can be avoided hereby.

Provisions may, furthermore, also be made in an especially preferred variant of a method according to the present invention for using a test gas-measuring device for carrying out steps f) through i). A test gas-measuring device is an impeccably functioning gas-measuring device, for which especially a response characteristic of the at least one sensor is known. In particular, a test gas-measuring device may be a new and/or already tested gas-measuring device. It can be achieved by using a test gas-measuring device that the determination of the flow time and/or of the waiting time can already be carried out reliably and accurately after one measurement. A plurality of measurements for the iterative determination of the flow time and/or of the waiting time can be avoided as a result. A test gas-measuring device may be used especially preferably to perform a first-time determination of the flow time and/or of the waiting time in case of a newly installed and/or converted test station. The determination of a suitable flow time and/or waiting time can be performed especially rapidly as a result for the reconfigured test station.

A method according to the present invention may be perfected especially preferably by the flow time being set as a difference of the test time and the waiting time. If a functioning gas-measuring device is detected in step i), detection of test gas took place at least during the test time. Since a waiting time is determined especially essentially by the gas-measuring device being used, this waiting time may be considered as a result to be at least essentially constant for the particular gas-measuring device. An especially effective determination of a flow time can therefore be provided by forming the difference between the test time and the waiting time. When a method according to the present invention is carried out again, sufficient feed of test gas can be ensured during the flow time by the reset flow time and the waiting time. It is, of course, also possible to take into account if a detection of the test gas by the gas-measuring device was already determined by the gas-measuring device during an analysis of the measurement results in step i) during a time that is shorter than the test time. The new flow time can also be set in this case as a difference between this shorter time and the waiting time. An even better adapted, especially shorter flow time and, as a result, an even lower test gas consumption can be provided hereby.

Furthermore, provisions may be made in a method according to the present invention for the feed of the at least one test gas to the interface in step g) to be carried out in pulses. Feeding in pulses means especially that the feed of the at least one test gas does not take place continuously, but time periods during which the test gas is being fed are interrupted by time periods during which the test gas is not being fed. A reduction of the total test gas consumption and, as a result, a cost reduction can thus be achieved.

A method according to the present invention may also be perfected such that the start and/or the duration of at least one of the pulses is set based on a result of the analysis performed in step i). What can be used here is the circumstance that a sensor signal or a sensor response of a sensor of a gas-measuring device is mostly continuous when a test gas is present, being either continuously rising or continuously falling. A deviation from this continuous characteristic may indicate the absence of test gas at the interface or in the fluid-communicating connection to the gas-measuring device. If such a deviation is detected, a pulse of the test gas feed can be triggered and/or the duration of a pulse can be adapted, especially prolonged, in this case. An especially need-adapted feed of test gas can be ensured hereby. In particular, it can be ensured hereby that when a method according to the present invention is carried out, the test gas consumption can also be reduced even if the flow time was set incorrectly and especially if an excessively long flow time was set.

According to a second aspect of the present invention, the object is accomplished by a test station for portable gas-measuring devices, wherein the test station has at least one interface for the fluid-communicating arrangement and signal-communicating arrangement of the gas-measuring device, and wherein the test station is configured to feed at least one test gas to the interface. A test station according to the present invention is characterized in that the test station is configured for carrying out a method according to the first aspect of the present invention. All features and advantages that were described in connection with a method according to the first aspect of the present invention will thus also be obtained for a test station that is configured for carrying out such a method according to the first aspect of the present invention.

Further, provisions are preferably made in a test station according to the present invention for the test station to have a control unit. The control unit being configured to actuate at least one component of the test station for carrying out the method according to the first aspect of the present invention. Such a control unit may be arranged, for example, in the interior of the test station. As an alternative, a control unit according to the present invention may also be a computer, which is arranged separately from the rest of the test station, there being, at least temporarily, a data connection between the control unit and the rest of the test station. A control unit may be used, in operative connection with signal-communicating arrangement of the gas-measuring device, for example, to carry out the detection of the type of the gas-measuring device to be tested and/or to set the flow time and the waiting time. Controlling, especially controlling and/or regulating, the feed of the test gas may also be provided by the control unit. To make it possible to provide these possibilities of use, the control unit is configured to actuate at least one component of the test station. Components that can be used when carrying out a method according to the present invention, for example, in the interface and/or in a gas feed unit of the test station, are considered to be components according to the present invention. The carrying out of a method according to the first aspect of the present invention can thus be made possible in an especially simple manner by a corresponding actuation of the at least one component.

According to an especially preferred variant of a test station according to the present invention, provisions may, furthermore, be made for the at least one component to be a feed device and/or a sensor. Feed of the test gas to the interface is made possible in the test station by a feed device, usually via an internal feed line. A sensor may be used in a test station according to the present invention especially for monitoring this feed. The sensor may preferably be configured for this, for example, as a flow sensor or as a pressure sensor and be arranged, further, at the internal feed line. Feed of the test gas in the test station can thus be controlled, especially controlled and/or regulated, in an especially simple and reliable manner by actuating a component, which is configured as a feed device and/or as a sensor.

Further measures improving the present invention appear from the following description of exemplary embodiments of the present invention, which are shown in the figures. All the features and/or advantages resulting from the claims, the description and the drawings, including design details and arrangements in space, may be essential for the present invention in themselves and in various combinations. Elements having the same function and mode of operation are designated by the same reference numbers in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
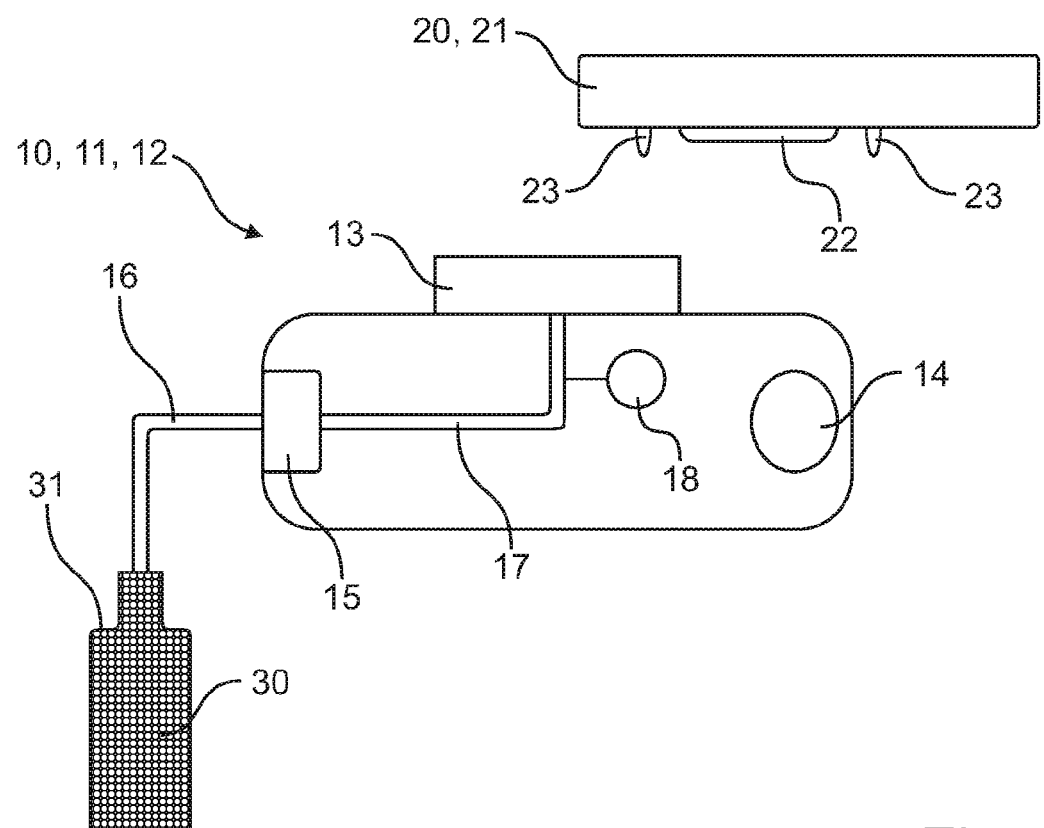
FIG. 1 is a schematic view of a test station according to the present invention and a gas-measuring device.

Referring to the drawings, FIG. 1 shows a test station 10 with a configuration 11 and in a state 12 and, further, a gas-measuring device 20 to be tested. The gas-measuring device 20 is not yet arranged at the test station 10. The test station 10 has especially an interface 13, in which the gas-measuring device 20 can be arranged. Thus, the interface 13 provides a coupling between the test station 10 and the gas-measuring device 20 to be tested. The gas-measuring device 20 is configured for feeding a test gas 30 to this interface 13. The test station 10 shown has for this a feed device 15, which is connected via feed lines 16, 17 to both a gas cylinder 31, which contains the test gas 30, and the interface 13. The feed lines 16, 17 are divided into external feed lines 16, i.e., feed lines 16 between the test station 10 and the gas cylinder 31, and internal feed lines 17, i.e., feed lines 17 located in the interior of the test station 10. Furthermore, a sensor 18, which is preferably configured as a flow sensor or as a pressure sensor, is arranged at the internal feed line 17. A determination of a mass flow of the test gas 30, which is fed to the interface 13, is thereby provided. Further, the test station 10 also has a control unit 14, which is configured, for example, for controlling the test station 10 for carrying out a method according to the present invention. Such a control unit 14 may also be arranged in the gas-measuring device 20, such that the gas-measuring device 20 and the test station 10 each have a control unit 14. The control unit 14 may also be configured as an external computer (neither a control unit as a part of the gas-measuring device 20 nor as an external computer is being shown). The control unit 14 is operatively connected to the interface 13 and is configured for actuating components of the test station 10, for example, for actuating the sensor 18 and/or the feed device 15. The carrying out of a method according to the present invention can thus be effected or at least supported by the control unit 14. The configuration 11 of the test station 10 comprises, for example a least one test gas feed configuration comprising a length of the feed lines 16, 17, where the lengths of the external feed lines 16 may, in particular, be different in different set-ups of a test station 10 according to the present invention. A state 12 of the test station 10 may comprise, for example, information on which gas-measuring devices 20 have already been tested or whether test gas 30 is already present in the feed lines 16, 17.

The gas-measuring device 20 is characterized especially by a gas-measuring device type 21. This type 21 may comprise information on, for example, the at least one installed sensor 22 of the gas-measuring device 20. Such information may be, for example, detectable test gases 30, a response characteristic or a state of aging of the sensor 22 of the gas-measuring device 20 to be tested. The gas-measuring device 20 has, further, an opposite interface 23, which facilitates the arrangement of the gas-measuring device 20 at the interface 13 of the test station 10.

Figure 2:
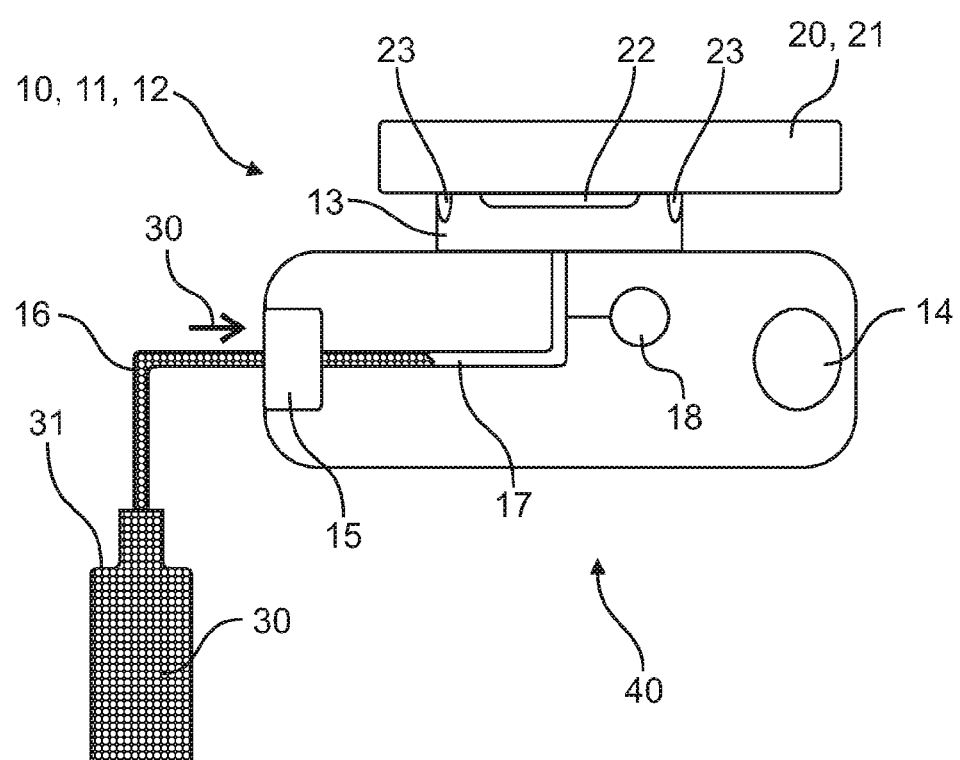
FIG. 2 is a schematic view of a test station according to the present invention and a gas-measuring device during step c) of a method according to the present invention.

FIG. 2 shows the test station 10, wherein the gas-measuring device 20 has been arranged via its opposite interface 23 at the interface 13 in a step a) of a method according to the present invention. As a result, a fluid-communicating connection is established between the interface 13 and the gas-measuring device 20, especially the sensor 22 of the gas-measuring device 20 and an electrical, signal connection is established between the gas-measuring device 20 and the control unit 14 via the interface 13. A test gas 30 thus flow via the interface 13 to the gas-measuring device 20. A type 21 of the gas-measuring device 20 was already detected in a step a) of a method according to the present invention by the test station 10, especially by the control unit 14 receiving a signal from the gas-measuring device 20 indicating the type. A flow time 40 and a waiting time 41 are correspondingly set in a step b) of a method according to the present invention, based on the detected gas-measuring device type 21. Shown in FIG. 2 are the test station 10 and the gas-measuring device 20 during the performance of a step c) of a method according to the present invention. The test gas 30, shown by an arrow, is fed in this step c) by the feed device 15 via the feed lines 16, 17 and sent to the interface 13. The flow time 40 is preferably set so as to have a duration of time that ensures that the test gas 30 will reach the interface 13. As an alternative or in addition to the flow time 40, a quantity of test gas 30 that is to be fed to the interface 13 may be set in the sense of the present invention. This quantity may be monitored, for example, with a sensor 18.

Figure 3:
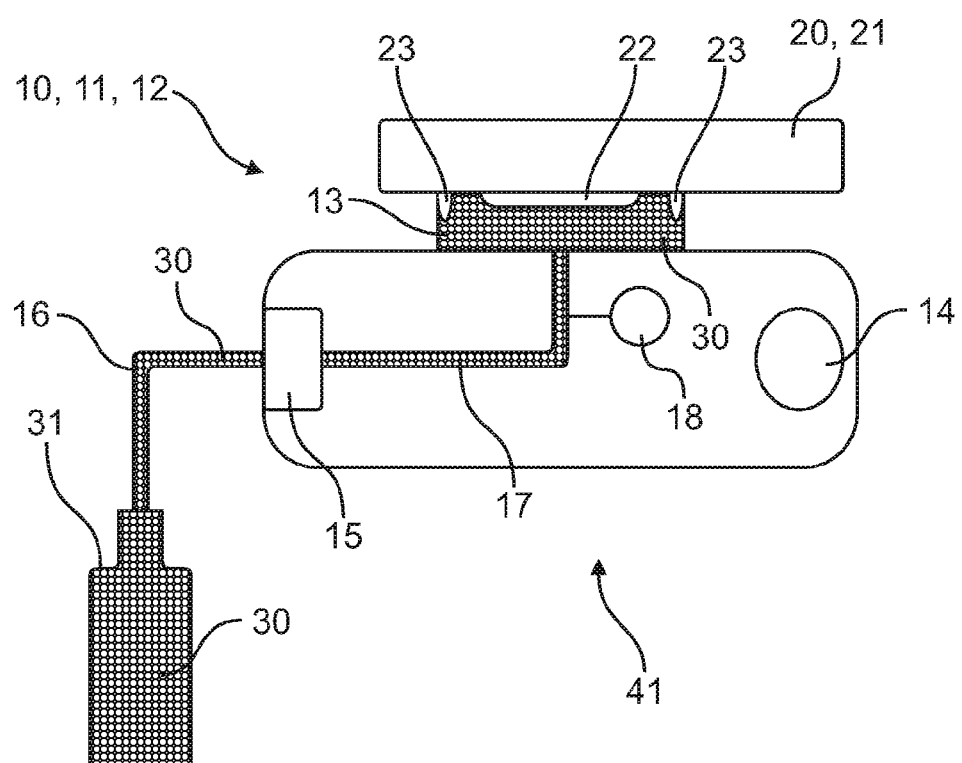
FIG. 3 is a schematic view of a test station according to the present invention and a gas-measuring device during step d) of a method according to the present invention.

This is shown in FIG. 3, in which the flow time 40 has ended. Feed of the test gas 30 by the feed device 15 is likewise ended. The test gas 30 is located in the interface 13 and can thus be detected by the sensor 22 of the gas-measuring device 20. A waiting time 41 is provided for this detection process, which is carried out according to the present invention during a step d) of a method according to the present invention. The measurement necessary for the detection process may be carried out at any time during the waiting time 41, especially also at the end shortly before the end of the waiting time 41. A plurality of measurements, distributed over the waiting time 41, may, in particular, also be provided. As an alternative, an individual, continuous measurement may also be carried out for the entire duration of the waiting time 41. Since no test gas 30 is fed during the waiting time 41, the consumption of test gas 30 during the performance of a test of a gas-measuring device 20 by a test station 10 can also be markedly reduced. This is especially true compared to tests of gas-measuring device 20 according to the state of the art, which tests require a continuous feed of test gas 30 before and especially also during a measurement and thus cause a high consumption of test gas 30. By providing the test gas 30 at the end of the flow time 40 in or at the interface 13, all the requirements that are necessary for a test of the gas-measuring device 20, especially of the sensor 22 of the gas-measuring device 20, are met. Consequently, reliable information can be obtained on the functioning of the gas-measuring device 20 in a step e) of a method according to the present invention by an analysis of the measurement performed during the waiting period (time) 41. The gas-measuring device 20 is marked as functioning in case of a successful detection of the test gas 30 by the gas-measuring device 20, and it is marked as defective in case of an unsuccessful detection.

Figure 4:
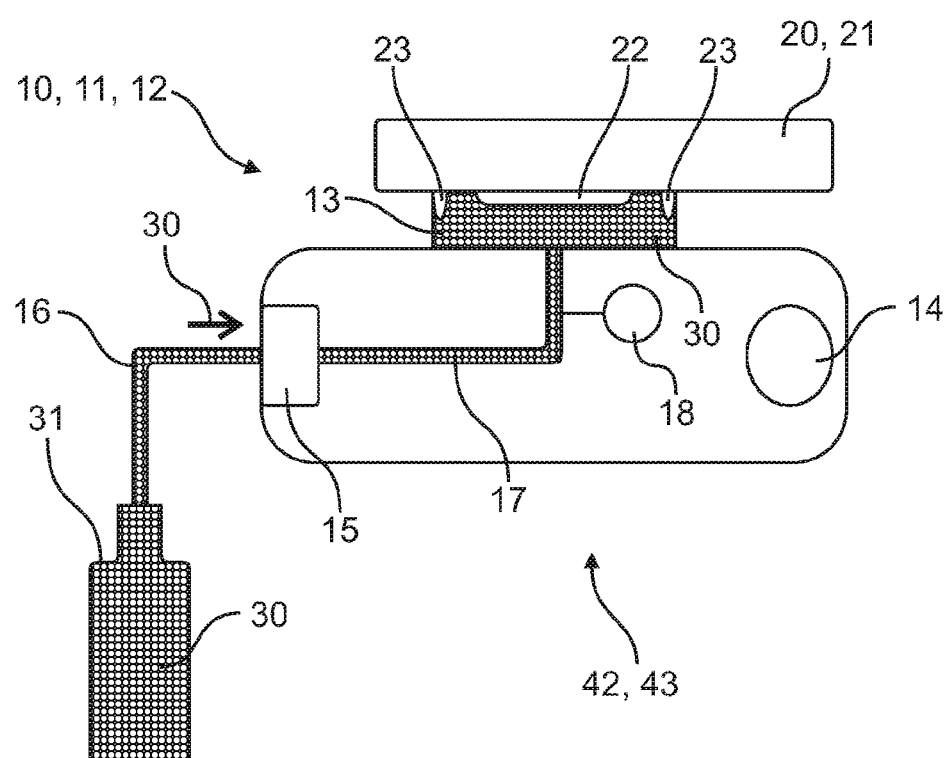
FIG. 4 is a schematic view of a test station according to the present invention and a gas-measuring device during steps g) and h) of a method according to the present invention.

FIG. 4 shows a possible variant of a test station 10 according to the present invention and of a method according to the present invention. If failure of detection of a test gas was observed during the analysis of the measurement results in step e) of a method according to the present invention, this can also be attributed to the lack of test gas 30 in or at the interface 13, in addition to a defective gas-measuring device 20. This may be due to a flow time 40 being too short (not shown). To rule this out, provisions may be made for carrying out a new test of the gas-measuring device 20 by the test station 10. The test gas 30 is fed during a test time 42, indicated by an arrow. This test time 42 may be set, for example, as a sum of the flow time 40 and the waiting time 41 (not shown), which were used in the last test. An even longer defined duration 42 may also be provided. Since feed of the test gas 30 is not ended even after a flow time 40, but test gas 30 can continue to be fed to the interface 13 for the entire test time 42, an effect of a flow time 40 being too short on a test result during the testing of the gas-measuring device 20 can be ruled out. Provisions may preferably also be made in this case for the feed of the test gas 30 to be carried out in pulses 43 rather than continuously. On the one hand, even though recurring feed of the test gas 30 to the interface 13 can be ensured as a result at least during some phases, increased consumption of test gas 30 can at least be minimized. The occurring pulses 43 may also be set by a feedback with results of the measurement by a sensor 22. An especially adapted feed of the test gas 30 can be provided as a result. In particular, a better setting of the flow time 40 and of the waiting time 41 may also be carried out iteratively by an analysis of the tests thus performed on the gas-measuring device 20. These improved flow times 40 and waiting times 41 can then be used for later tests of this gas-measuring device 20 with the test station 10. It is possible as a result to carry out the method according to the present invention and to operate a test station 10 according to the present invention in an especially need-adapted or need-based manner.

Figure 5:
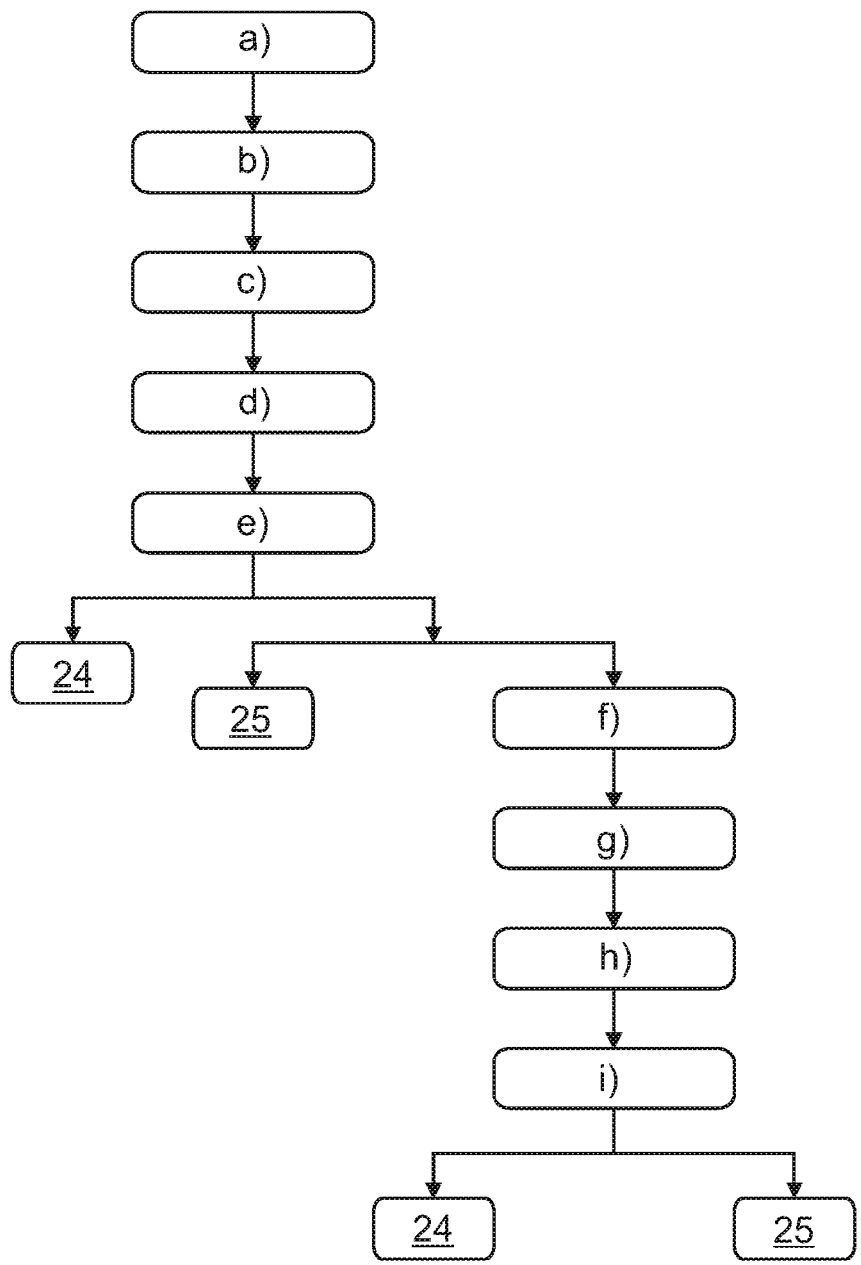
FIG. 5 is a flow diagram of the method according to the present invention.

FIG. 5 shows a schematic view of a possible global course of a method according to the present invention. The devices used to carry out the method and their features are not shown here. According to a method according to the present invention, a gas-measuring device 20 is arranged in a first step a) at an interface 13 of a test station 10. A fluid-communicating connection is established and a signal-communicating connection is established by this arrangement between the interface 13 and the gas-measuring device 20. Further, the type 21 of the gas-measuring device 20 to be tested is detected by the test station 10 in this first step a). Based especially on this detected type 21 of the gas-measuring device 20 to be tested, a flow time 40, during which the test gas 30 is fed through the test station 10, and a waiting time 41, during which no test gas 30 is being fed, are set in a step b) of a method according to the present invention. Feed of a test gas 30 through the test station 10 is then started in the next step c) for feeding the test gas 30 to the interface 13. This feed is carried out over the duration of the flow time 40 and is ended after the end of the flow time 40. The flow time 40 was preferably set in step b) to be so long that test gas 30 is present at and/or in the interface 13 after the end of the flow time 40 and hence after the conclusion of the feed. A measurement is subsequently performed in a step d) of a method according to the present invention to detect the fed test gas 30 by the gas-measuring device 20 for the duration of the waiting time 41. As a conclusion of a core of a method according to the present invention, a result of this measurement carried out in step d) is analyzed in a last step e). This may preferably be carried out by the test station 10, but also by the gas-measuring device 20 itself. If the test gas 30 was successfully detected in step d) by the gas-measuring device 20, a functioning state 24 of the gas-measuring device 20 to be tested can be determined in step e). If this is not the case, a defective state 25 of the gas-measuring device 20 to be tested can be determined in step e). As an alternative, additional steps f) through i) may also be carried out in a variant of a method according to the present invention. Thus, a test time 42 is set in step f). This test time 42 may be set, for example, as a sum of the flow time 40 and waiting time 41 set in step b). Feed of the test gas 30 is subsequently started in step g), and this feed is continued for the duration of the test time 42. A measurement is carried out by the gas-measuring device 20 in step h) simultaneously in at least some phases to detect the fed test gas 30. The results of this measurement are then analyzed, in turn, in a step i) of a method according to the present invention. A functioning 24 or possibly defective state 25 of a gas-measuring device 20 to be tested can then be determined as the end result. It can be achieved, in particular, by the additional steps f) through i) of this variant of a method according to the present invention that a defective state is not assigned erroneously to gas-measuring devices 20 that have a functioning state 24, especially if this assignment can be attributed to a flow time 40 set as an excessively short time.

While specific embodiments of the invention have been shown and described in detail to illustrate the application of the principles of the invention, it will be understood that the invention may be embodied otherwise without departing from such principles.

APPENDIX

| | |
|---|---|
| 10 | Test station |
| 11 | Configuration |
| 12 | State |
| 13 | Interface |
| 14 | Control unit |
| 15 | Feed device |
| 16 | External feed line |
| 17 | Internal feed line |
| 18 | Sensor |
| 20 | Gas-measuring device |
| 21 | Type |
| 22 | Sensor |
| 23 | Opposite interface |
| 24 | Functioning state |
| 25 | Defective state |
| 30 | Test gas |
| 31 | Gas cylinder |
| 40 | Flow time |
| 41 | Waiting time |
| 42 | Test time |
| 43 | Pulse |

What is claimed is:

1. A method for operating a test station for portable gas-measuring devices, wherein the test station comprises at least one interface for a fluid-communicating arrangement of the gas-measuring device and is configured for feeding at least one test gas to the at least one interface, the method comprising the steps of:

arranging a gas-measuring device at the at least one interface;

detecting a type of the gas-measuring device to be tested by the test station;

setting a flow time, during which the at least one test gas is fed through the test station, and setting a waiting time, during which the at least one test gas is not fed, based on a result of the step of detecting the type of the gas-measuring device;

starting a feed of the at least one test gas to feed the at least one test gas via the at least one interface to the gas-measuring device, for a duration of the flow time, through the test station;

starting the waiting time and performing a measurement to detect the at least one fed test gas by the gas-measuring device, after an end of the flow time and after an end of the feed of the at least one test gas and before an end of the waiting period; and analyzing results of the measurement by the test station or by the gas-measuring device or by both the test station and the gas-measuring device.

2. A method in accordance with claim 1, wherein the step of detecting a type of the gas-measuring device comprises detecting at least one feature from the group of features comprising:

a sensor of the gas-measuring device;

a response characteristic of at least one sensor of the gas-measuring device;

a state of aging of at least one sensor of the gas-measuring device; and a test gas that is needed or a test gas that is used or both a test gas that is needed and a test gas that is used.

3. A method in accordance with claim 1, wherein the step of setting the flow time and the waiting time is based on a configuration of the test station or a state of the test station or both a configuration of the test station and a state of the test station.

4. A method in accordance with claim 1, wherein the measurement is carried out at least partly by the gas-measuring device while the at least one test gas is being fed via the at least one interface to the gas-measuring device.

5. A method in accordance with claim 1, wherein the measurement results are compared with at least one reference value during the step of analyzing results of the measurement.

6. A method in accordance to claim 5, wherein the gas-measuring device is marked as defective with at least one reference value during the step of analyzing results of the measurement.

7. A method in accordance with claim 6, wherein in case of the negative result of the comparison the method further comprises:

setting of a test time during which the at least one test gas is fed through the test station;

starting of a feed of the at least one test gas to feed the test gas via the at least one interface to the gas-measuring device for the duration of the test time by the test station;

carrying out a measurement to detect the at least one test gas fed by the gas-measuring device during the test time; and analyzing results of the measurement to detect the at least one test gas fed by the gas-measuring device during the test time.

8. A method in accordance with claim 7, wherein the test time set and a result of the analyzing results of the measurement to detect the at least one test gas fed by the gas-measuring device during the test time are taken into account when setting the flow time in a repeated feed of at least one test gas to feed the at least one test gas via the at least one interface to the gas-measuring device, for a duration of the flow time.

9. A method in accordance with claim 8, wherein the test time set and a result of the analyzing results of the measurement to detect the at least one test gas fed by the gas-measuring device during the test time are taken into account when setting a next waiting time.

10. A method in accordance with claim 9, wherein the flow time is set as a difference between the test time and the waiting time in a repeated starting of the waiting time and a repeated performing of a measurement to detect the at least one fed test gas by the gas-measuring device.

11. A method in accordance with claim 7, wherein the feed of the at least one test gas via the at least one interface to the gas-measuring device for the duration of the test time by the test station is carried out in pulses.

12. A method in accordance with claim 11, wherein a start or a duration or both a start and a duration of at least one of the pulses is set based on the step of analyzing results of the measurement to detect the test gas fed by the gas-measuring device during the test time.

13. A test station for portable gas-measuring devices, the test station comprising:
   at least one interface for a fluid-communicating arrangement of a gas-measuring device;
   at least one test gas feed configuration comprising a feed device for feeding at least one test gas to the at least one interface;
   control unit connected to the feed device and configured to:
   detect a type of the gas-measuring device to be tested that is arranged at the at least one interface;
   set a flow time, during which the at least one test gas is fed through the test station, and set a waiting time, during which the at least one test gas is not fed, based on a result of detecting the type of the gas-measuring device;
   start a feed of the at least one test gas to feed the at least one test gas, with the feed device and via the at least one interface, to the gas-measuring device to be tested that is arranged at the at least one interface, for a duration of the flow time, through the test station;
   start the waiting time and performing a measurement to detect the at least one fed test gas by the gas-measuring device, after an end of the flow time and after an end of the feed of the at least one test gas and before an end of the waiting period; and
   analyze results of the measurement by the test station.

14. A test station in accordance with claim 13, wherein the control unit is configured for actuating the feed device such that the feed of the at least one test gas via the at least one interface to the gas-measuring device for a duration of the test time by the test station is carried out in pulses after determining that the gas-measuring device is defective, wherein the gas-measuring device is determined to be defective due to the results of the measurement being analyzed.

15. A test station in accordance with claim 14, wherein a start or a duration or both a start and a duration of at least one of the pulses is set based on the analyzing results of the measurement.

16. A test station in accordance with claim 14, further comprising a sensor.

* * * * *